United States Patent
Yanai et al.

(10) Patent No.: US 11,371,636 B2
(45) Date of Patent: Jun. 28, 2022

(54) GAS SUPPLY SOCKET

(71) Applicants: ANEST IWATA CORPORATION, Yokohama (JP); KOMATSU-SEIKI CO., LTD., Yokohama (JP)

(72) Inventors: Hiroyuki Yanai, Yokohama (JP); Tatsuya Sekino, Yokohama (JP); Yoshihiro Kamimura, Yokohama (JP)

(73) Assignees: Anest Iwata Corporation, Yokohama (JP); Komatsu-Seiki Co., Ltd., Yokohama (JP)

( * ) Notice: Subject to any disclaimer, the term of this patent is extended or adjusted under 35 U.S.C. 154(b) by 69 days.

(21) Appl. No.: 16/631,559

(22) PCT Filed: Jul. 27, 2017

(86) PCT No.: PCT/JP2017/027307
§ 371 (c)(1),
(2) Date: Jan. 16, 2020

(87) PCT Pub. No.: WO2019/021434
PCT Pub. Date: Jan. 31, 2019

(65) Prior Publication Data
US 2020/0173592 A1    Jun. 4, 2020

(51) Int. Cl.
*F16L 37/407*    (2006.01)
*F16L 37/60*    (2006.01)
(Continued)

(52) U.S. Cl.
CPC .......... *F16L 37/407* (2013.01); *A61G 12/005* (2013.01); *A61M 16/0816* (2013.01);
(Continued)

(58) Field of Classification Search
CPC ......... F16L 37/407; F16L 37/33; F16L 37/60; A61G 12/005; A61M 39/26; Y10T 137/698; Y10T 137/6984
See application file for complete search history.

(56) References Cited

U.S. PATENT DOCUMENTS 2,386,270 A * 10/1945 Samiran ................ F16L 37/407
251/149.6
2,742,052 A *  4/1956 McKee ................ A61M 16/10
137/329.1
(Continued)

FOREIGN PATENT DOCUMENTS

FR    2 431 649 A1    2/1980
FR    2 995 654 A1    3/2014
(Continued)

OTHER PUBLICATIONS

English translation of International Preliminary Report on Patentability (Chapter I) (Application No. PCT/JP2017/027307) dated Feb. 6, 2020, 9 pages.
(Continued)

*Primary Examiner* — David Colon-Morales
(74) *Attorney, Agent, or Firm* — Burr & Brown, PLLC

(57) ABSTRACT

There is provided a gas supply socket which can ensure sealing between an outer cylinder and an inner cylinder even when the inner cylinder, inclined with respect to the outer cylinder, is placed in the outer cylinder. The gas supply socket 10 includes an outer cylinder 11, an inner cylinder 12, a movable body 20 disposed within the outer cylinder 11, and a valve body 18 and a valve seat portion 19 provided within the inner cylinder 12. An intermediate cylinder 13 is provided between the outer cylinder 11 and the inner cylinder 12. When the inner cylinder 12, inclined with respect to the outer cylinder 11, is placed in the outer cylinder 11, the
(Continued)

inner cylinder 12 and the intermediate cylinder 13 tilt with respect to the outer cylinder 11.

4 Claims, 7 Drawing Sheets

(51) Int. Cl.
    *A61G 12/00*     (2006.01)
    *A61M 16/08*     (2006.01)
    *A61M 16/20*     (2006.01)
    *A61M 39/26*     (2006.01)

(52) U.S. Cl.
    CPC ........... *A61M 16/208* (2013.01); *F16L 37/60* (2013.01); *A61M 39/26* (2013.01)

(56) References Cited

U.S. PATENT DOCUMENTS

| | | | | |
|---|---|---|---|---|
| 2,771,308 A * | 11/1956 | Hemeyer | F16L 37/42 |
| | | | 251/74 |
| 2,905,487 A * | 9/1959 | Schifter | F16K 15/044 |
| | | | 137/630.22 |
| 2,908,511 A * | 10/1959 | Rogers | F16L 37/60 |
| | | | 137/329.1 |
| 3,004,777 A * | 10/1961 | Buonaccorsi | A61G 12/004 |
| | | | 285/64 |
| 3,170,667 A * | 2/1965 | Szohatzky | F16L 37/407 |
| | | | 251/149.6 |
| 3,441,046 A * | 4/1969 | Cranage | F16K 51/00 |
| | | | 137/329.1 |
| 3,477,105 A | 11/1969 | Cranage | | |
| 3,532,101 A * | 10/1970 | Snyder, Jr. | F16K 17/40 |
| | | | 137/75 |
| 3,563,267 A * | 2/1971 | Thompson | F16L 37/60 |
| | | | 137/329.1 |
| RE28,334 E * | 2/1975 | Cranage | F16L 37/084 |
| | | | 137/360 |
| 3,931,829 A * | 1/1976 | McWhinnie, Jr. | A61M 16/20 |
| | | | 137/329.1 |
| 4,114,853 A * | 9/1978 | Medvick | F16L 37/23 |
| | | | 251/149.6 |
| 4,123,089 A * | 10/1978 | Viero | F16L 37/084 |
| | | | 285/39 |
| 4,190,075 A * | 2/1980 | Kayser | F16K 15/18 |
| | | | 137/329.1 |
| 4,354,523 A * | 10/1982 | Hochmuth | F16L 29/007 |
| | | | 137/322 |
| 4,509,554 A * | 4/1985 | Failla | F16L 29/04 |
| | | | 137/329.1 |
| 4,527,587 A * | 7/1985 | Fairlamb | F16L 29/02 |
| | | | 137/329.3 |
| 6,189,560 B1 * | 2/2001 | Reynolds | F16L 37/60 |
| | | | 137/360 |
| 2019/0240401 A1* | 8/2019 | List | A61M 5/14248 |

FOREIGN PATENT DOCUMENTS

| | | |
|---|---|---|
| GB | 1 503 302 A | 3/1978 |
| JP | 2013-096499 A1 | 5/2013 |
| WO | 00/20793 A1 | 4/2000 |

OTHER PUBLICATIONS

International Search Report and Written Opinion (Application No. PCT/JP2017/027307) dated Oct. 24, 2017.

* cited by examiner

GAS SUPPLY SOCKET

TECHNICAL FIELD

Embodiments of the present invention relate to a gas supply socket for use in a medical outlet apparatus for supplying a medical gas such as oxygen gas, laughing gas, aspirating gas, or air.

BACKGROUND ART

Conventionally, a plurality of gas supply sockets for medical gases such as oxygen gas, laughing gas and air, and a gas supply socket into which suction is introduced, are installed e.g. in the wall of a treatment room or an ordinary ward. An attachment plug, corresponding to each gas supply socket, is inserted into the socket as necessary (see, for example, patent document 1).

Such a gas supply socket includes an outer cylinder to which a gas supply source is connected, and an inner cylinder which is detachably provided in the outer cylinder and in which a valve seat and a valve body are housed. The socket is provided with an operating member which, when an attachment plug is inserted into the inner cylinder, moves the valve body to detach it from the valve seat.

CITATION LIST

Patent Literature

Patent document 1: Japanese Patent Laid-Open Publication No. 2013-96499

SUMMARY OF THE INVENTION

Problems to be Solved by the Invention

The outer cylinder of the above-described gas supply socket is embedded in the wall of a room. The inner cylinder is pulled out of the outer cylinder as necessary for replacement or repair of the inner cylinder.

However, it is difficult to accurately place the inner cylinder in the outer cylinder; the inner cylinder can sometimes be inclined with respect to the outer cylinder.

In such a case, a sealing structure between the outer cylinder and the inner cylinder may become imperfect, resulting in leakage of a gas, supplied from a supply source, into the room via the inner cylinder.

Embodiments of the present invention have been made in view of the above situation. It is therefore an object of the present invention to provide a gas supply socket which can ensure sealing between an outer cylinder and an inner cylinder even when the inner cylinder, inclined with respect to the outer cylinder, is placed in the outer cylinder.

Means for Solving the Problems

The present invention, in one embodiment, provides a gas supply socket comprising: an outer cylinder; a movable body disposed slidably within the outer cylinder and biased by a first elastic body; an inner cylinder provided slidably within the outer cylinder and contactable with the movable body, and internally having a valve seat portion; a spherical valve body which is contactable with the valve seat portion in the inner cylinder; a second elastic body, provided within the inner cylinder, for biasing the valve body toward the valve seat portion; an intermediate cylinder interposed between the outer cylinder and the inner cylinder; an inner seal provided between the inner cylinder and the intermediate cylinder; and an outer seal provided between the intermediate cylinder and the outer cylinder.

In an embodiment of the present invention, when the inner cylinder is pulled out of the outer cylinder and the intermediate cylinder, the movable body is pressed by the first elastic body and comes into contact with the inner seal of the intermediate cylinder, thereby forming a hermetic sealing structure.

In an embodiment of the present invention, the inner seal includes a first seal portion and a second seal portion, and the outer seal is located between the first seal portion and the second seal portion in the axial direction.

In an embodiment of the present invention, an operating member which, when an attachment plug is inserted into the inner cylinder, moves the valve body against the force of the second elastic body, thereby detaching the valve body from the valve seat portion, is provided within the inner cylinder.

The present invention, in another embodiment, provides a resin frame having a through-hole, in which an inner cylinder is to be inserted into the through-hole such that the inner cylinder projects from one side of the frame, and a reference pin, including a pin head and a pin body, is to be mounted to the frame such that it projects in the same direction as the inner cylinder, wherein said resin frame includes a pin mounting portion to which the reference pin is to be mounted, and wherein a protrusion is provided on one side of the pin mounting portion from which the reference pin projects, and a tapered groove is provided on the other side of the pin mounting portion.

In an embodiment of the present invention, a groove into which the pin head is to be fitted is provided around the protrusion on the one side of the pin mounting portion.

Advantageous Effects of the Invention

According to the embodiments of the present invention, the intermediate cylinder is interposed between the outer cylinder and the inner cylinder. Even when the inner cylinder, inclined with respect to the outer cylinder, is placed in the outer cylinder, the inclination of the inner cylinder can be absorbed by tilting the inner cylinder and the intermediate cylinder with respect to the outer cylinder. This can enhance sealing between the outer cylinder and the inner cylinder.

DESCRIPTION OF THE EMBODIMENTS

First Embodiment

Figure 1:
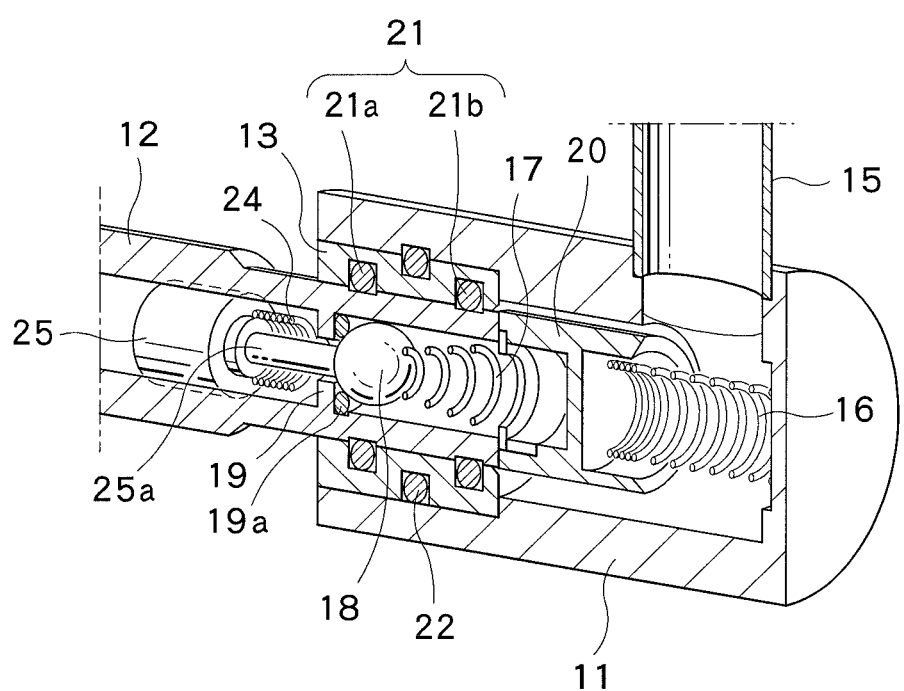
FIG. 1 is a diagram showing a positional relationship between an outer cylinder and an inner cylinder in a gas supply socket according to a first embodiment of the present invention.

A medical gas pipe connecting apparatus 1, including a gas supply socket 10 according to a first embodiment of the present invention, will now be described with reference to FIGS. 1 through 4. The medical gas pipe connecting apparatus 1 is installed e.g. in the wall of a treatment room or an ordinary ward, and includes the gas supply socket 10, and an attachment plug 3 which is to be detachably mounted in the gas supply socket 10 and to which a tube 4 is coupled.

A medical gas is introduced from a supply source into the gas supply socket 10. For example, a supply source of oxygen gas as a medical gas is connected to the gas supply socket 10 of this embodiment.

As described above, the attachment plug 3 is to be inserted into the gas supply socket 10.

The gas supply socket 10 will now be described. As shown in FIGS. 1 through 4, the gas supply socket 10 includes an outer cylinder 11 connected via a communication pipe 15 to an oxygen gas supply source (not shown), a movable body 20 disposed slidably within the outer cylinder 11 and pressed by a first spring (first elastic body) 16 provided in the outer cylinder 11, and an inner cylinder 12 provided slidably within the outer cylinder 11 and which is contactable with the movable body 20.

A valve seat portion 19 having an O-ring 19a is provided in the inner cylinder 12. Further, a spherical valve body 18 which is to contact the O-ring 19a of the valve seat portion 19 to hermetically seal the valve seat portion 19 is provided within the inner cylinder 12.

Further, a second spring (second elastic body) 17 for biasing the valve body 18 toward the valve seat portion 19 is installed in the inner cylinder 12.

An intermediate cylinder 13 is interposed between the outer cylinder 11 and the inner cylinder 12. The inner cylinder 12 is configured to be capable of being pulled out of the outer cylinder 11 and the intermediate cylinder 13. When pulling the inner cylinder 12 out of the outer cylinder 11 and the intermediate cylinder 13, the first spring 16 provided in the outer cylinder 11 pushes the movable body 20 toward the inner cylinder 12. In particular, as shown in FIG. 1, the movable body 20 slides toward the inner cylinder 12, and the left end of the movable body 20 comes into contact with the below-described second seal portion 21b of the intermediate cylinder 13 to hermetically seal the interior of the outer cylinder 11 (not illustrated).

An inner seal 21, composed of a first seal portion 21a and the second seal portion 21b, is provided between the inner cylinder 12 and the intermediate cylinder 13, and an outer seal 22 is provided between the outer cylinder 11 and the intermediate cylinder 13. The first seal portion 21a and the second seal portion 21b, constituting the inner seal 21, are each an annular elastic body such as an O-ring. The gap between the inner cylinder 12 and the intermediate cylinder 13 is hermetically sealed by disposing the inner seal 21 in the inner surface of the intermediate cylinder 13. The outer seal 22 is an annular elastic body such as an O-ring. The gap between the intermediate cylinder 13 and the outer cylinder 11 is hermetically sealed by disposing the outer seal 22 in the outer surface of the intermediate cylinder 13.

The outer seal 22 is located between the first seal portion 21a and the second seal portion 21b of the inner seal 21 in the axial direction.

Referring to FIG. 1, the intermediate cylinder 13 can tilt with respect to the outer cylinder 11 in three-dimensional directions with the outer seal 22 as a supporting point. Thus, when the inner cylinder 12 is placed in the outer cylinder 11, with the axis of the inner cylinder 12 slightly inclined with respect to the axis of the outer cylinder 11, the intermediate cylinder 13 and the inner cylinder 12 slightly tilt with respect to the outer cylinder 11. Since the gap between the outer cylinder 11 and the intermediate cylinder 13 is hermetically sealed with the outer seal 22, a hermetic sealing structure can be ensured between the outer cylinder 11 and the intermediate cylinder 13 even when the intermediate cylinder 13 and the inner cylinder 12 thus tilt slightly. A hermetic sealing structure is also formed between the inner cylinder 12 and the intermediate cylinder 13 by the inner seal 21 comprised of the first seal portion 21a and the second seal portion 21b.

Figure 4:
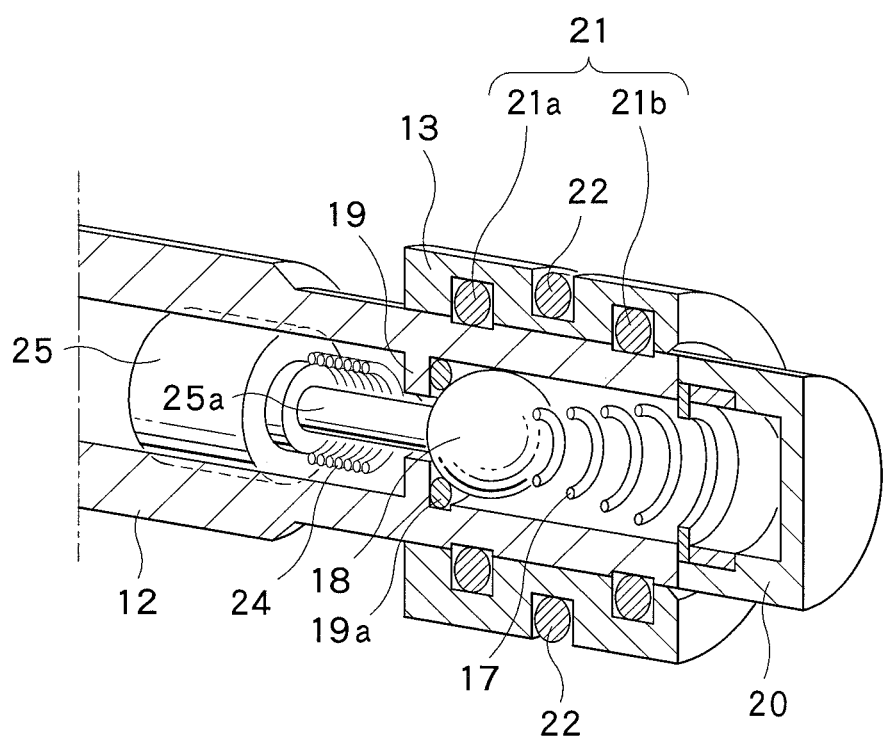
FIG. 4 is an enlarged view showing the internal structure of the outer cylinder and the inner cylinder.
Figure 5:
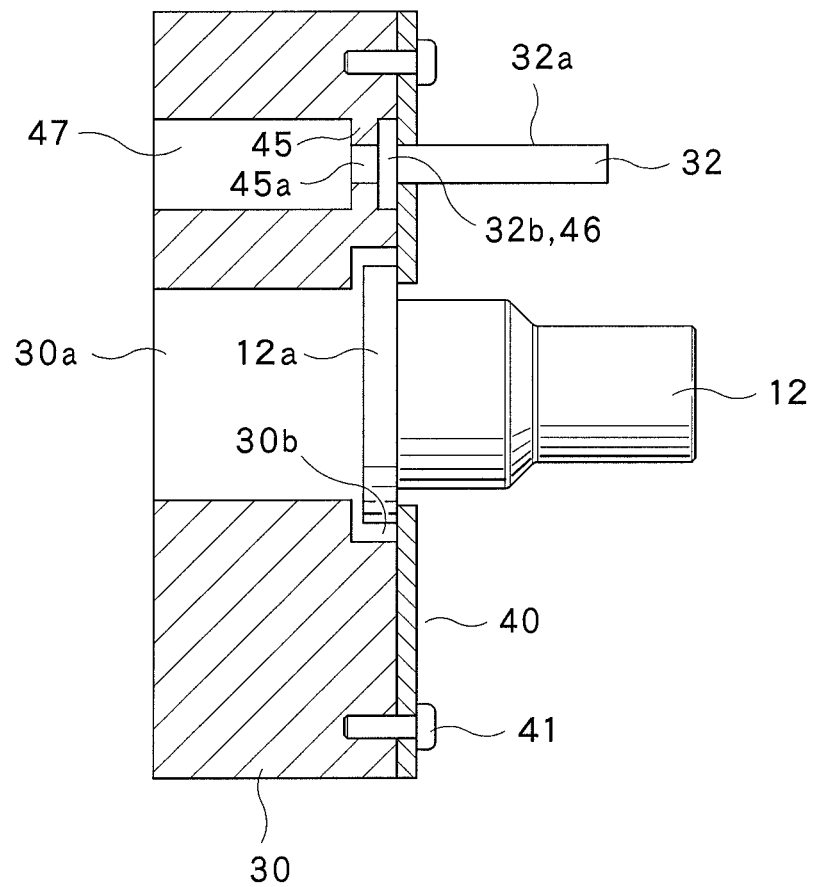
FIG. 5 is a cross-sectional view of a resin frame for holding the inner cylinder according to a second embodiment of the present invention.
Figure 6A:
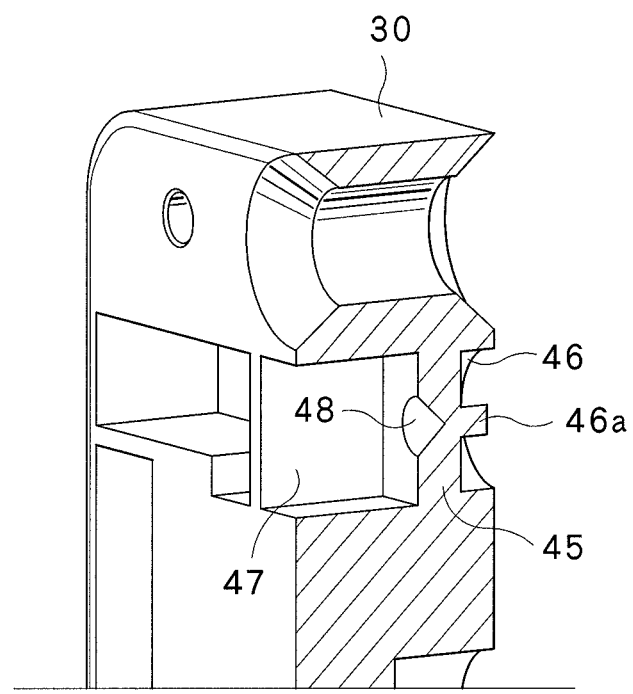
FIG. 6A is a perspective view of a portion of the resin frame.
Figure 6B:
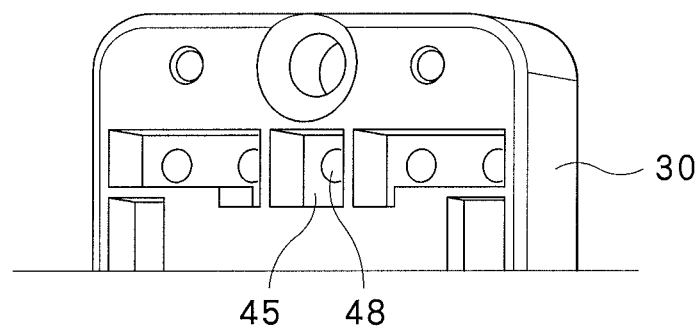
FIG. 6B is a perspective view of the front side of the resin frame.
Figure 6C:
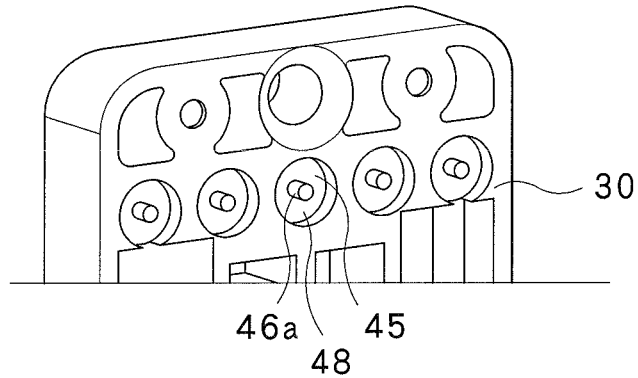
FIG. 6C is a perspective view of the back side of the resin frame.

As shown in FIG. 4, an operating member 25 which, when inserting the attachment plug 3 into the inner cylinder 12, is pressed by the attachment plug 3 and presses on the valve body 18, is slidably provided within the inner cylinder 12. The operating member 25 includes an operating pin 25a which is contactable with the valve body 18. The operating member 25 is continually biased outward (leftward in FIG. 4) by a third spring (third elastic body) 24. When inserting the attachment plug 3 into the inner cylinder 12, the attachment plug 3 presses on the operating member 25, and the operating pin 25a of the operating member 25 presses on the valve body 18 against the force of the second spring 17, thereby detaching and thus releasing the valve body 18 from the valve seat portion 19.

A mounting structure for mounting the gas supply socket 10 to a wall will now be described with reference to FIGS. 2 and 3.

A mounting plate 35 for installing the outer cylinder 11 in the wall is mounted to the outer end (left end in FIG. 2) of the outer cylinder 11 of the gas supply socket 10. The right-side portion of the gas supply socket 10 is embedded into the wall by means of the mounting plate 35. The mounting plate 35 is disposed on the surface of the wall, and a decorative plate 36 having an opening 36a is mounted to the mounting plate 35. The surface of the gas supply socket 10 (e.g. the surface of the decorative plate 36 and the surface of the below-described face plate 37) may be coated with an antibacterial material.

A resin frame 30 holding the inner cylinder 12 is placed in the opening 36a of the decorative plate 36. A face plate 37 is mounted to the outer end (left end in FIG. 2) of the resin frame 30. The attachment plug 3 is held by a plug holder 3a. The attachment plug 3, held by the plug holder 3a, is inserted through an opening 37a of the face plate 37 into the inner cylinder 12.

The resin frame 30 is equipped with a plurality of reference pins 32 that extend in the same direction as the inner cylinder 12. The reference pins 32 are inserted through the opening 36a of the decorative plate 36 into openings 39 of the mounting plate 35.

The reference pins 32 of the resin frame 30 are inserted into the openings 39 of the mounting plate 35 only when the inner cylinder 12, held by the resin frame 30, is an appropriate one; when the inner cylinder 12 is an inappropriate one, the reference pins 32 do not meet the openings 39 of the mounting plate 35 and will hit the mounting plate 35.

Thus, only an appropriate resin frame 30 can be mounted in the mounting plate 35 and the decorative plate 36, whereas an inappropriate resin frame 30 cannot be mounted in the mounting plate 35 and the decorative plate 36.

The operation of the gas supply socket 10 of this embodiment will now be described.

When making replacement or a repair of the inner cylinder 12 of the gas supply socket 10, the inner cylinder 12 held by the resin frame 30, together with the resin frame 30 and the face plate 37, is pulled out of the outer cylinder 11.

As the inner cylinder 12 is pulled out, the first spring 16 which has been pressed and compressed by the inner cylinder 12 expands, and the movable body 20 is pressed by the spring 16 and moves toward the intermediate cylinder 13, and comes into contact with the second seal portion 21b of the intermediate cylinder 13, thereby hermetically sealing the interior of the outer cylinder 11. Accordingly, oxygen gas which has been transported through the communication pipe 15 from the oxygen gas supply source remains in the outer cylinder 11 and is not discharged from the intermediate cylinder 13 to the outside.

Next, a new repaired inner cylinder 12, together with the resin frame 30 and the face plate 37, is inserted through the opening 36a of the decorative plate 36 into the outer cylinder 11.

The inner cylinder 12 which has been inserted into the outer cylinder 11 comes into contact with the movable body 20 and presses on the movable body 20 toward the communication pipe 15 (see FIG. 1). The movable body 20 moves toward the communication pipe 15 while compressing the first spring 16, whereby the movable body 20 leaves the intermediate cylinder 13. The hermetic sealing structure between the movable body 20 and the intermediate cylinder 13 is thus released.

On the other hand, the spherical valve body 18 provided in the inner cylinder 12 is pressed by the second spring 17 against the O-ring 19a of the valve seat portion 19, whereby a hermetic sealing structure is formed between the valve body 18 and the valve seat portion 19. The inner cylinder 12 is thus placed in the outer cylinder 11.

The inner cylinder 12 is sometimes placed in the outer cylinder 11, with the axis of the inner cylinder 12 slightly inclined with respect to the axis of the outer cylinder 11. In such a case, the intermediate cylinder 13 and the inner cylinder 12 slightly tilt with respect to the outer cylinder 11. Nevertheless, a hermetic sealing structure can be ensured between the outer cylinder 11 and the intermediate cylinder 13, because the gap between the outer cylinder 11 and the intermediate cylinder 13 is hermetically sealed with the outer seal 22.

The gap between the inner cylinder 12 and the intermediate cylinder 13 becomes hermetically sealed with the inner seal 21 composed of the first seal portion 21a and the second seal portion 21b.

When placing the inner cylinder 12 in the outer cylinder 11, the reference pins 32, extending from the resin frame 30 in the same direction as the inner cylinder 12, are inserted into the openings 39 of the mounting plate 35. This makes it possible to confirm that the inner cylinder 12, which has been placed in the outer cylinder 11, is an appropriate one.

Figure 2:
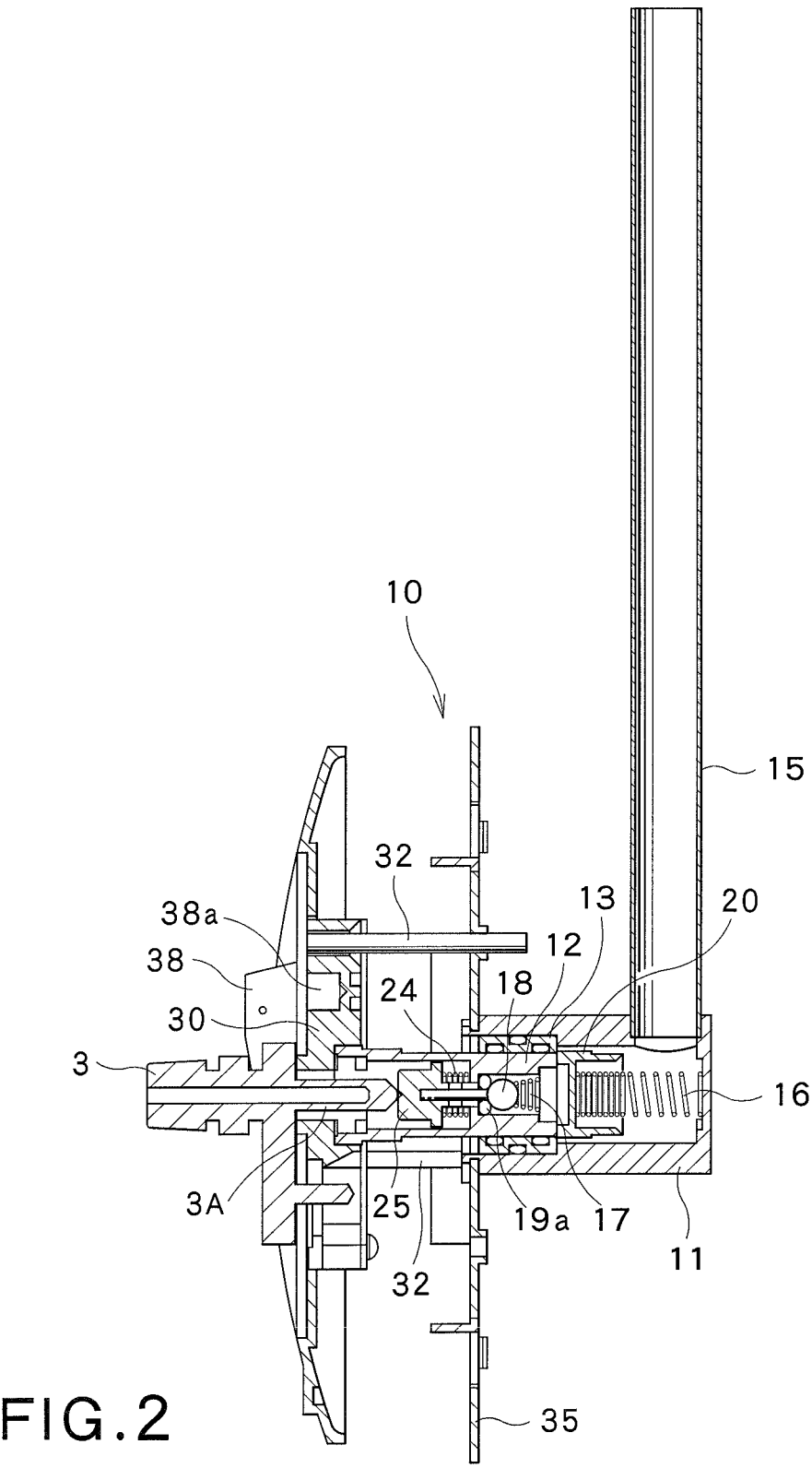
FIG. 2 is a cross-sectional side view of a medical gas pipe connecting apparatus including the gas supply socket.
Figure 3:
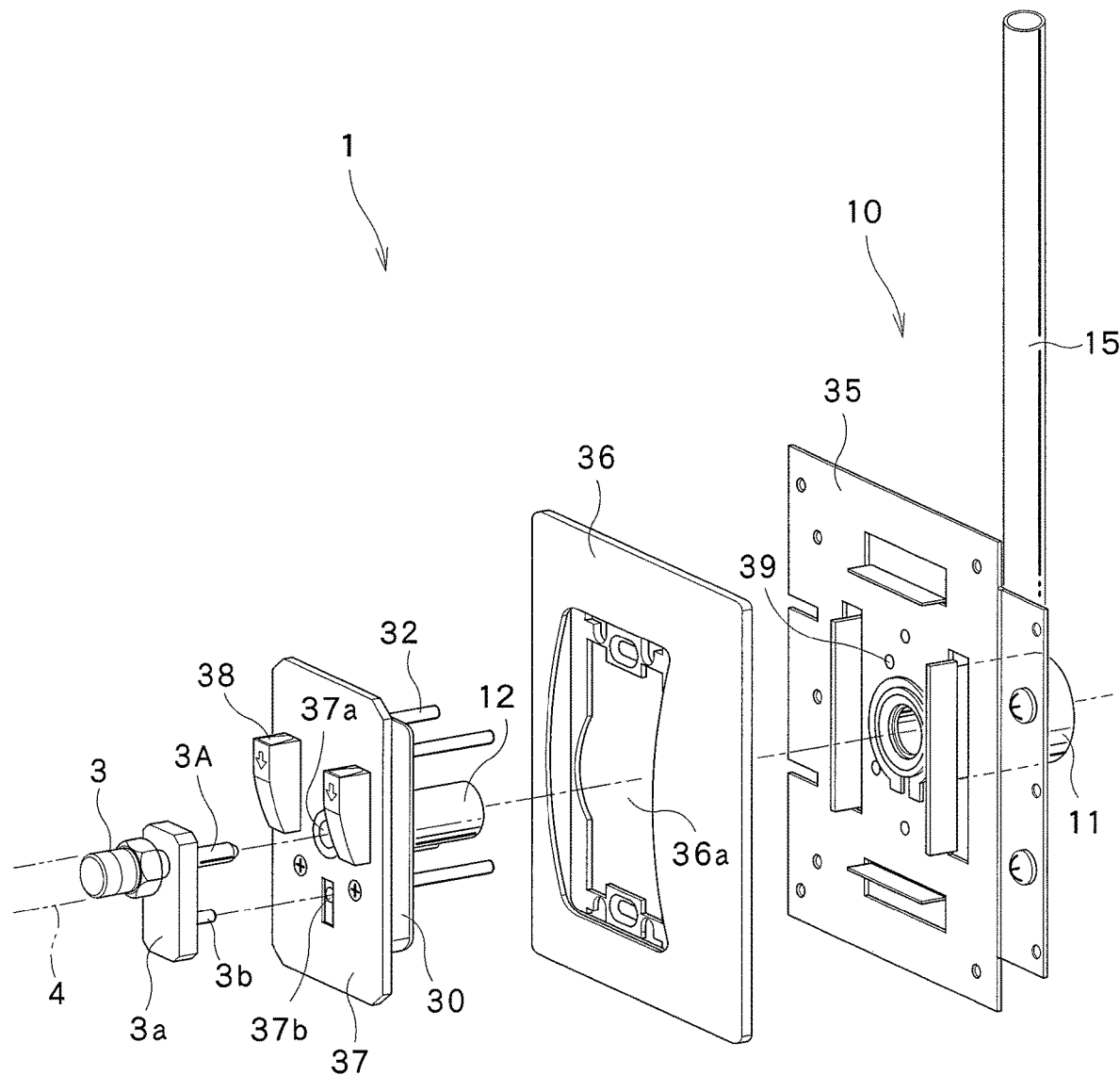
FIG. 3 is a schematic perspective view of the medical gas pipe connecting apparatus including the gas supply socket.

Before using the gas supply socket 10, a projecting pipe 3A of the attachment plug 3, held by the plug holder 3a, is inserted from the side of the face plate 37 into the inner cylinder 12 as shown in FIGS. 2 and 3. At the same time, a pin 3b which projects from the plug holder 3a toward the face plate 37 is inserted into an opening 37b provided in the face plate 37. This makes it possible to insert only the projecting pipe 3A of an appropriate attachment plug 3 into the inner cylinder 12.

In the case of an inappropriate attachment plug 3, the position of the pin 3b of the plug holder 3a does not coincide with the position of the opening 37b of the face plate 37, and therefore the pin 3b hits the face plate 37. Accordingly, the projecting pipe 3A of the attachment plug 3 cannot be inserted into the inner cylinder 12.

Thus, according to this embodiment, only the projecting pipe 3A of an appropriate attachment plug 3 can be inserted into the inner cylinder 12 by inserting the pin 3b of the plug holder 3a into the opening 37b of the face plate 37.

The projecting pipe 3A of the attachment plug 3 that has been inserted into the inner cylinder 12 presses on the operating member 25 disposed within the inner cylinder 12. The operating member 25 moves toward the valve body 18 against the force of the third spring 24, and the operating pin 25a of the operating member 25 presses on the valve body 18. The valve body 18 moves toward the movable body 20 against the force of the second spring 17 and leaves the valve seat portion 19, whereby the hermetic sealing between the valve seat portion 19 and the valve body 18 is released.

Accordingly, oxygen gas from the oxygen gas supply source can be supplied through the communication pipe 15 into the outer cylinder 11, and can be securely supplied to the user via the inner cylinder 12, the attachment plug 3 and the tube 4.

According to the above-described embodiment, the intermediate cylinder 13, provided with the inner seal 21 and the outer seal 22, is interposed between the outer cylinder 11 and the inner cylinder 12. Even when the inner cylinder 12, inclined with respect to the outer cylinder 11, is placed in the outer cylinder 11, the inclination of the inner cylinder 12 can be absorbed by tilting the inner cylinder 12 and the intermediate cylinder 13 with respect to the outer cylinder 11. This can enhance sealing between the outer cylinder 11 and the inner cylinder 12.

Second Embodiment

A second embodiment of the present invention will now be described with reference to FIG. 5 and FIGS. 6A through 6C.

The second embodiment shown in FIG. 5 and FIGS. 6A through 6C relates to a mounting structure of the inner cylinder 12 of the gas supply socket 10 and a mounting structure of the resin frame 30 for holding the inner cylinder 12.

As shown in FIG. 5 and FIGS. 6A through 6C, the inner cylinder 12 of the gas supply socket 10 is held by the resin frame 30. The resin frame 30 has a through-hole 30a having, in a one-side portion of the circumferential wall, a circumferential groove 30b.

On the other hand, the inner cylinder 12, at its one end, a flange portion 12a which is disposed in the circumferential groove 30b of the through-hole 30a.

A locking plate 40 for locking the flange portion 12a of the is inner cylinder 12 is mounted on the one side of the resin frame 30. The locking plate 40 is mounted to the resin frame 30 by mounting bolts 41.

Further, the above-described reference pins 32 that extend in the same direction as the inner cylinder 12 are mounted to the one side of the resin frame 30. The reference pins 32 are to be inserted into the openings 39 of the mounting plate 35 only when an appropriate inner cylinder 12 is placed in the outer cylinder 11 (see FIG. 3).

Each reference pin 32 includes a pin body 32a and a pin head 32b.

The resin frame 30 before mounting thereto of the inner cylinder 12 and the reference pins 32 will now be described.

The resin frame 30 before assembly has pin mounting portions 45 to which the reference pins 32 are to be mounted. The pin mounting portion 45 refers to that area of the resin frame 30 to which each reference pin 32 is to be mounted. Each pin mounting portion 45, on its one side from which the reference pin 32 projects, has a groove 46 into which the pin head 32b of the reference pin 32 is to be fitted. A protrusion 46a is formed in the groove 46. The pin mounting portion 45, on the other side, has a tapered groove 48 and a space 47.

The operation of the resin frame 30 of this embodiment will now be described.

First, the resin frame 30 before assembly is produced by molding. The resin frame 30 before assembly is a resin body having a plurality of pin mounting portions 45 each having the protrusion 46a, but not having the below-described opening 45a. The resin frame 30 before assembly is produced by using a mold. Next, a pin mounting portion(s) 45 to which the reference pin(s) 32 is to be mounted is selected from the plurality of pin mounting portions 45 of the molded resin frame 30. In each selected pin mounting portion 45, an opening 43a is formed by means of a drill from the tapered groove 48 formed on the other side of the pin mounting portion 45.

Upon the formation of the opening 45a, the protrusion 46a in the groove 46 is removed by the drill. With the tapered groove 48 provided on the other side of the pin mounting portion 45, the opening 45a can be formed smoothly with high accuracy from the tapered groove 48 by using the drill.

Next, the inner cylinder 12 is inserted into the through-hole 30a of the resin frame 30 so that the flange portion 12a of the inner cylinder 12 is housed in the circumferential groove 30b.

In a separate process from the process for mounting the inner cylinder 12, the pin head 32b of the reference pin 32 is placed in the groove 46 of the selected pin mounting portion 45, the locking plate 40 is placed on the one side of the resin frame 30, and the locking plate 40 is fixed by the mounting bolts 41.

By thus mounting the locking plate 40 to the resin frame 30, the inner cylinder 12 and the reference pin 32 can be firmly fixed to the resin frame 30 by means of the locking plate 40.

As described above, a pin mounting portion(s) 45 to which the reference pin(s) 32 is to be mounted is selected, and the opening(s) 45a is formed in the selected pin mounting portion(s) 45. Thus, the protrusion(s) 46a remains in the groove(s) 46 of the non-selected pin mounting portion(s) 45; therefore, the reference pin(s) 32 cannot be mounted to the non-selected pin mounting portion(s) 45.

In the above-described embodiment, the pin head 32b of the reference pin 32 is disposed in the groove 46 provided on the one side of a selected pin mounting portion 45. However, it is also possible to insert the reference pin 32 into the opening 45a of a pin mounting portion 45 from the space 47, and to engage a nut (not shown) with the pin body 32a from the one side of the pin mounting portion 45, thereby mounting the reference pin 32 to the pin mounting portion 45.

According to the embodiment described above, the resin frame 30 before assembly, having a plurality of pin mounting portions 45 each having the protrusion 46a, but not having the opening 45a, is produced e.g. by molding, and thereafter the opening(s) 45a is formed with a drill at a desired place to remove the protrusion 46a. The reference pin 32 can thus be mounted to a desired pin mounting portion 45 by the simple additional processing involving the formation of the opening 45a by drilling. This can increase the productivity of the resin frame 30 having the reference pin(s) 32.

A variation of the above-described embodiment will now be described with reference to FIGS. 7A through 7C. The variation shown in FIGS. 7A through 7C relates to a resin frame 30 to which a reference pin(s) 32, penetrating the resin frame 30, is mounted. The other construction of the variation is approximately the same as that of the embodiment shown in FIG. 5 and FIGS. 6A through 6C.

Figure 7A:
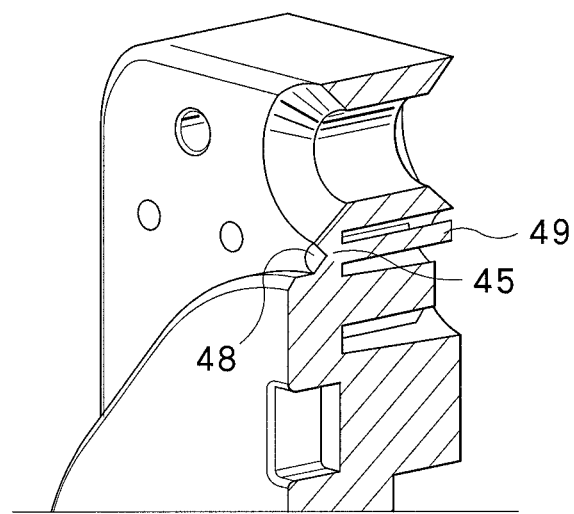
FIG. 7A is a perspective view of a variation of the resin frame.
Figure 7B:
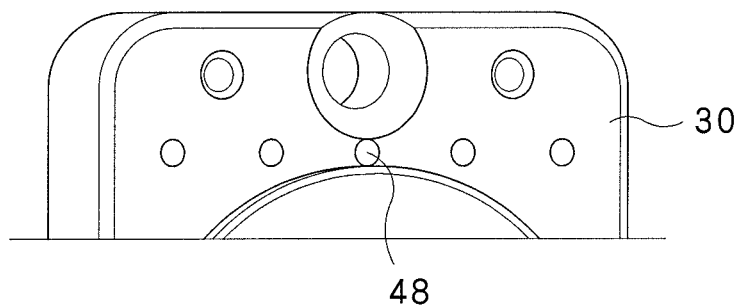
FIG. 7B is a perspective view of the front side of the variation of the resin frame.
Figure 7C:
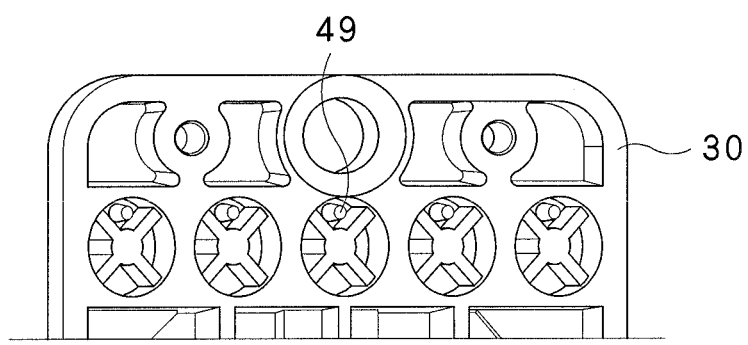
FIG. 7C is a perspective view of the back side of the variation of the resin frame.

In the variation shown in FIGS. 7A through 7C, the same symbols are used for the same components or elements as those of the embodiment shown in FIG. 5 and FIGS. 6A through 6C, and a detailed description thereof is omitted.

Referring to FIGS. 7A through 7C, the resin frame 30 has a plurality of pin mounting portions 45 to which the reference pins 32 are to be mounted. Each pin mounting portion 45, on its one side, has a protrusion 49 and, on the other side, has e.g. a tapered groove 48 as a pilot hole for additional processing.

The operation of the resin frame 30 of this variation will now be described.

First, the resin frame 30 before assembly, shown in FIGS. 7A through 7C, is produced by molding. Molding of the resin frame 30 before assembly can be performed in the same manner as that for the resin frame 30 before assembly according to the second embodiment. Next, a pin mounting portion(s) 45 to which the reference pin(s) 32 is to be mounted is selected from the plurality of pin mounting portions 45 of the molded resin frame 30. In each selected pin mounting portion 45, an opening 45a is formed by means of a drill from the tapered groove 48 formed on the other side of the pin mounting portion 45.

Upon the formation of the opening 45a, the protrusion 49 on the one side of the pin mounting portion 45 is removed by the drill. With the tapered groove 48 provided on the other side of the pin mounting portion 45, the opening 45a can be formed smoothly with high accuracy from the tapered groove 48 by using the drill.

Next, the inner cylinder 12 is inserted into the through-hole 30a of the resin frame 30 so that the flange portion 12a of the inner cylinder 12 is housed in the circumferential groove 30b.

Next, the locking plate 40 is placed on the one side of the resin frame 30, and the locking plate 40 is mounted by the mounting bolts 41.

By thus mounting the locking plate 40 to the resin frame 30, the inner cylinder 12 can be firmly fixed to the resin frame 30 by means of the locking plate 40.

The reference pin 32 can be mounted to the pin mounting portion 45 of the resin frame 30 by inserting the reference pin 32 into the opening 45a from the other side of the pin mounting portion 45, and engaging a nut (not shown) with the pin body 32a from the one side of the pin mounting portion 45.

As with the preceding embodiment, this variation can also increase the productivity of the resin frame 30 having the reference pin(s) 32.

While certain embodiments of the present invention have been described, these embodiments are not intended to limit the scope of the present invention. Various omissions, substitutions and changes in the form of the embodiments described herein may be made without departing from the spirit of the invention. The accompanying claims and their equivalents are intended to cover such forms or modifications as would fall within the scope and spirit of the invention.

DESCRIPTION OF THE SYMBOLS 1 medical gas pipe connecting apparatus
3 attachment plug
3A projecting pipe
10 gas supply socket
11 outer cylinder
12 inner cylinder
13 intermediate cylinder
15 communication pipe
16 first spring
17 second spring
18 valve body
19 valve seat portion
20 movable body
21 inner seal
21a first seal portion
21b second seal portion
22 outer seal
24 third spring
25 operating member
25a operating pin
30 resin frame
32 reference pin
32a pin body
32b pin head
35 mounting plate
36 decorative plate
37 face plate
38 stopper
40 locking plate
41 mounting bolt
45 pin mounting portion
46 groove
46a protrusion
48 tapered groove

The invention claimed is:

1. A gas supply socket comprising:
an outer cylinder;
a movable body disposed slidably within the outer cylinder and biased by a first elastic body;
an inner cylinder provided slidably within the outer cylinder and contactable with the movable body, and internally having a valve seat portion;
a spherical valve body which is contactable with the valve seat portion in the inner cylinder;
a second elastic body, provided within the inner cylinder, for biasing the valve body toward the valve seat portion;
an intermediate cylinder interposed between the outer cylinder and the inner cylinder;
an inner seal provided between the inner cylinder and the intermediate cylinder; and
an outer seal provided between the intermediate cylinder and the outer cylinder,
wherein the inner seal includes a first seal portion and a second seal portion, and the outer seal is located between the first seal portion and the second seal portion in an axial direction, and
wherein when an axis of the inner cylinder is inclined with respect of an axis of the outer cylinder, the intermediate cylinder and the inner cylinder tilt with respect to the outer cylinder.

2. The gas supply socket according to claim 1, wherein when the inner cylinder is pulled out of the outer cylinder and the intermediate cylinder, the movable body is pressed by the first elastic body and comes into contact with the inner seal of the intermediate cylinder, thereby forming a hermetic sealing structure.

3. The gas supply socket according to claim 2, wherein an operating member which, when an attachment plug is inserted into the inner cylinder, moves the valve body against the force of the second elastic body, thereby detaching the valve body from the valve seat portion, is provided within the inner cylinder.

4. The gas supply socket according to claim 1, wherein the first seal portion and the second seal portion are in contact with both the inner cylinder and the intermediate cylinder, and wherein the outer seal is in contact with both the intermediate cylinder and the outer cylinder.

* * * * *